US008777936B2

(12) United States Patent
Fischer et al.

(10) Patent No.: US 8,777,936 B2
(45) Date of Patent: Jul. 15, 2014

(54) COOLING SYSTEM FOR A CATHETER

(75) Inventors: Gerald Fischer, Vols (AT); Florian Hintringer, Ampass (AT); Martin Goll, Innsbruck (AT)

(73) Assignee: AFreeze GmbH, Hall in Tirol (AT)

( * ) Notice: Subject to any disclaimer, the term of this patent is extended or adjusted under 35 U.S.C. 154(b) by 1045 days.

(21) Appl. No.: 12/210,052

(22) Filed: Sep. 12, 2008

(65) Prior Publication Data
US 2009/0124972 A1 May 14, 2009

Related U.S. Application Data

(60) Provisional application No. 60/986,989, filed on Nov. 9, 2007.

(51) Int. Cl.
*A61B 18/18* (2006.01)
(52) U.S. Cl.
USPC .............................................. 606/21
(58) Field of Classification Search
USPC .............. 606/21, 22, 23, 24, 25, 26; 604/113, 604/114
See application file for complete search history.

(56) References Cited

U.S. PATENT DOCUMENTS

| | | | | |
|---|---|---|---|---|
| 5,667,505 A | * | 9/1997 | Straus | 606/24 |
| 5,758,505 A | * | 6/1998 | Dobak et al. | 62/6 |
| 6,530,920 B1 | * | 3/2003 | Whitcroft et al. | 606/13 |
| 2003/0149428 A1 | | 8/2003 | Ryba | |
| 2004/0049178 A1 | | 3/2004 | Abboud et al. | |
| 2004/0215295 A1 | | 10/2004 | Littrup et al. | |

FOREIGN PATENT DOCUMENTS

| | | |
|---|---|---|
| GB | 2360573 A | 9/2001 |
| WO | WO 98/06339 A1 | 2/1998 |
| WO | WO 0211638 A1 | 2/2002 |
| WO | WO0213710 A1 | 2/2002 |
| WO | WO02069820 A2 | 12/2002 |

OTHER PUBLICATIONS

EPO Communication Pursuant to Article 94(3) EPC, Jan. 3, 2013.

* cited by examiner

*Primary Examiner* — Manuel Mendez
(74) *Attorney, Agent, or Firm* — Robert A. Blaha; Smith Risley Tempel Santos LLC

(57) ABSTRACT

A cooling device for cooling a catheter, the cooling device comprising a main cooling unit adapted for supplying the catheter with a main cooling medium and a precooling unit adapted for precooling the main cooling medium before supply of the main cooling medium to the catheter, wherein the main cooling unit comprises a cooling pathway through which a fluid is guidable as the main cooling medium, and comprising a control unit adapted for automatically controlling the main cooling unit and the precooling unit to perform a predetermined cooling procedure, wherein the control unit is adapted for activating the precooling unit before activating a supply of the main cooling medium by the main cooling unit to the catheter.

17 Claims, 9 Drawing Sheets

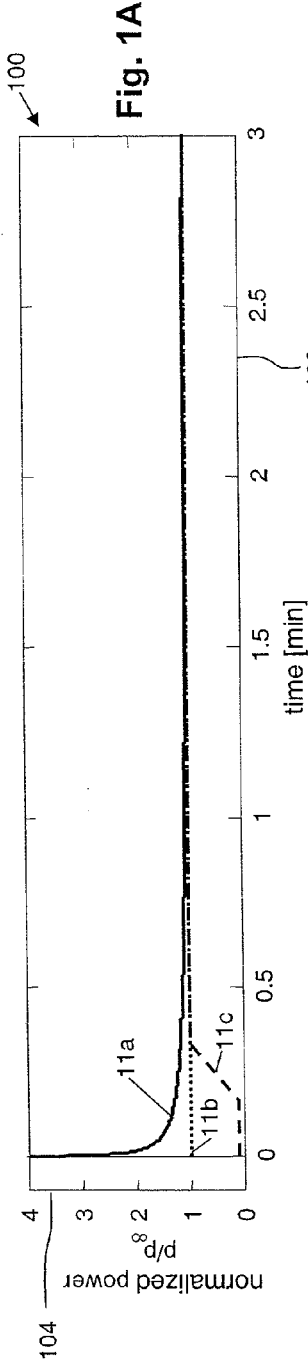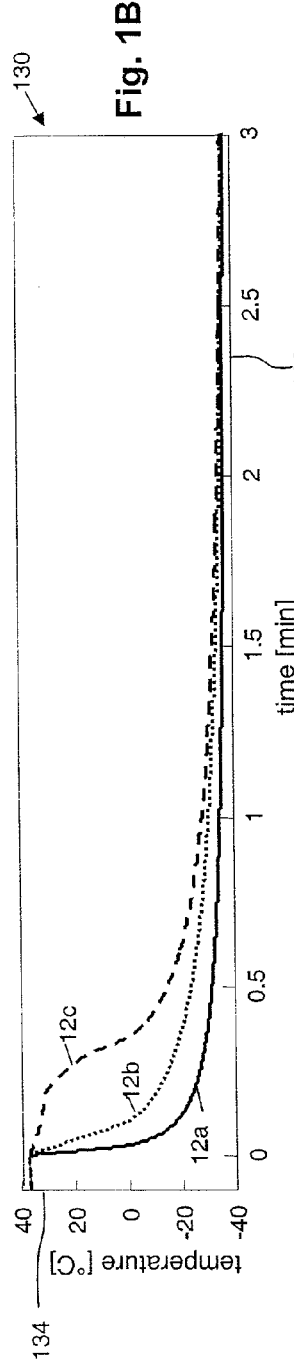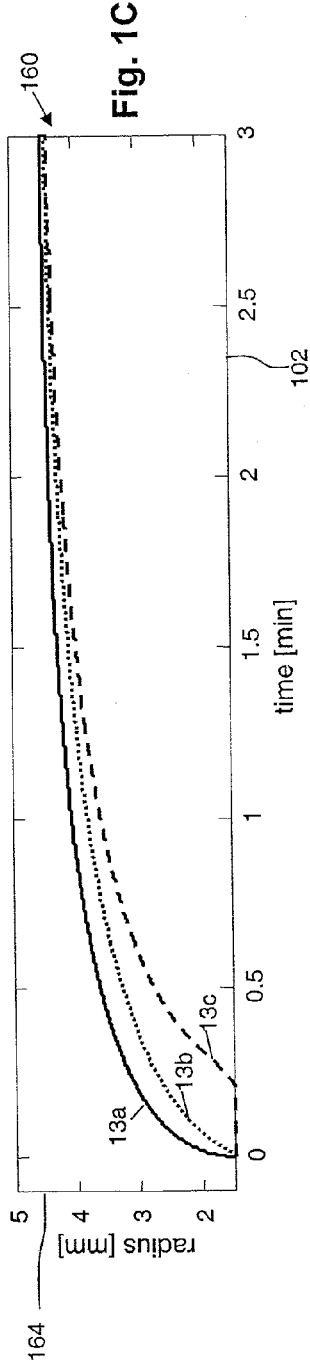

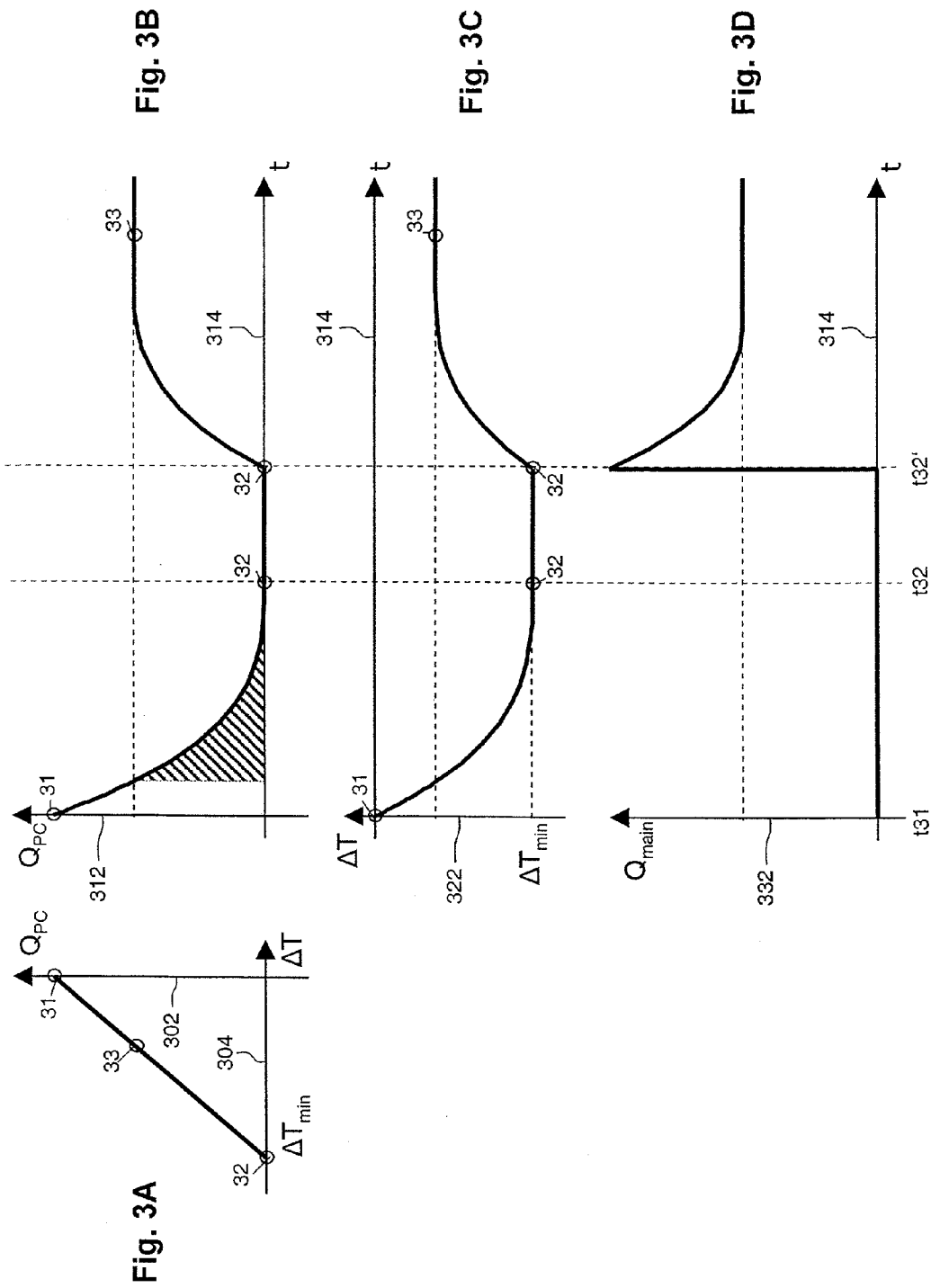

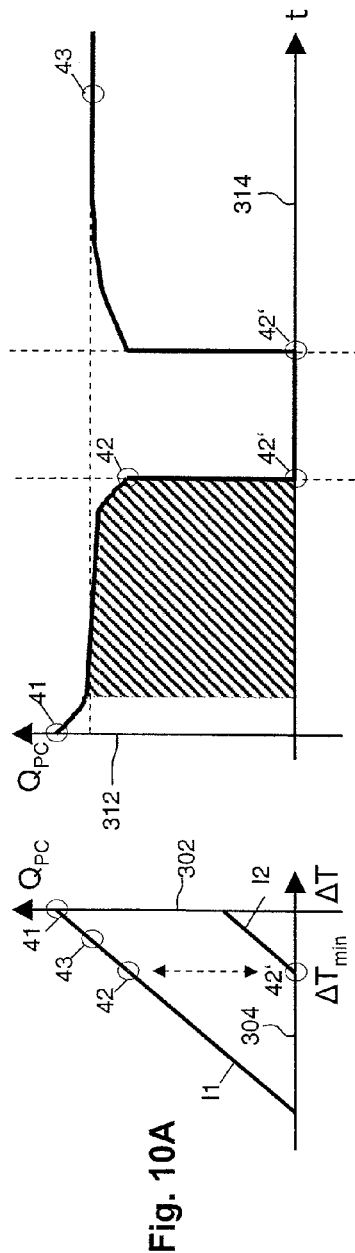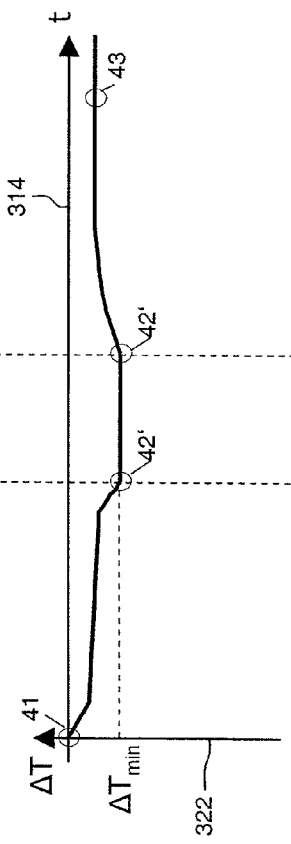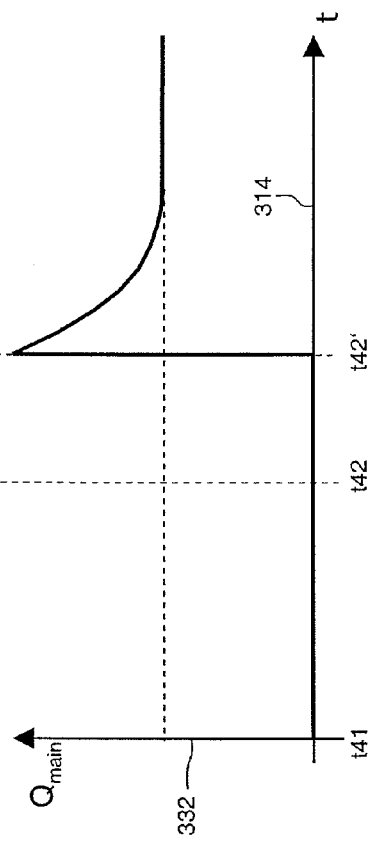

COOLING SYSTEM FOR A CATHETER

CROSS REFERENCE TO RELATED APPLICATION

This application claims the benefit of the filing date of U.S. Provisional Patent Application No. 60/986,989 filed Nov. 9, 2007, the disclosure of which is hereby incorporated herein by reference.

BACKGROUND

The invention relates to a cooling device for cooling a catheter.

The invention further relates to a cryosurgery system.

Moreover, the invention further relates to a method of cooling a catheter.

Cryosurgery is the application of extreme cold to destroy abnormal or diseased tissue. Cryosurgery works by taking advantage of the destructive force of freezing temperatures on cells. At low temperatures, ice crystals may form inside the cells, which can tear them apart. More damage may occur when blood vessels supplying the tissue freeze.

In cryosurgery and cyroablation, precooling a refrigerant may enable a more efficient use of a refrigerant. Less refrigerant may be needed, and smaller dimensions are possible. More freezing cycles can be obtained from a given amount of refrigerant. Less-boiling may be achieved in a supply line of the refrigerant.

The pressure of the primary refrigerant may vary with the ambient temperature. Thus, often a pressure reduction is carried out for operating the catheter at a defined pressure. In US 2003/0149428A1 a method is described for simultaneous precooling of the primary refrigerant below its boiling temperature at the selected pressure. Simultaneous control of pressure and temperature is termed conditioning.

U.S. Pat. No. 6,471,694 discloses an apparatus for automatic operation of a refrigeration system to provide refrigeration power to a catheter for tissue ablation or mapping. The primary refrigeration system can be open loop or closed loop, and a precool loop is a closed loop. Equipment and procedures are disclosed for bringing the system to the desired operational state, for controlling the operation by controlling refrigerant flow rate, for performing safety checks, and for achieving safe shutdown.

Other methods of precooling a primary refrigerant in cryosurgery by the use of a secondary refrigerant are disclosed in U.S. Pat. No. 5,758,505, U.S. Pat. No. 6,237,355, U.S. Pat. No. 6,530,234, U.S. Pat. No. 7,004,936, WO 02/069820 A2 and GB 2,360,573 A.

Furthermore, alternatively to a secondary refrigerant, a Stirling engine or a Peltier element may be used for precooling as described in US 2003/0149428A1 and WO 02/13710 A1.

SUMMARY

It is an object of the invention to enable an efficient catheter cooling.

In order to achieve the object defined above, a cooling device for cooling a catheter, a cryosurgery system, and a method of cooling a catheter according to the independent claims are provided.

According to an exemplary embodiment of the invention, a cooling device for cooling a catheter is provided, the cooling device comprising a main cooling unit adapted for supplying the catheter with a main cooling medium, a precooling unit adapted for precooling the main cooling medium before supply of the main cooling medium to the catheter, wherein the main cooling unit comprises a cooling pathway (which may also be denoted as a cooling loop) through which a fluid is guidable as the main cooling medium, and comprising a control unit adapted for automatically controlling the main cooling unit and the precooling unit to perform a predetermined cooling procedure, wherein the control unit is adapted for activating the precooling unit before activating a supply of the main cooling medium by the main cooling unit to the catheter.

According to another exemplary embodiment of the invention, a method of cooling a catheter is provided, the method comprising supplying the catheter with a main cooling medium, precooling the main cooling medium before supplying the main cooling medium to the catheter, guiding a fluid as the main cooling medium through a cooling loop (which may also be denoted as a cooling pathway), and activating the precooling before activating a supply of the main cooling medium to the catheter.

According to an exemplary embodiment of the invention, a cooling device for cooling a catheter (such as a catheter for cryosurgery or cyroablation) is provided, the cooling device comprising a main cooling unit (or a primary cooling unit) adapted for supplying the catheter with a main cooling medium (such as a circulating or streaming refrigerant) and a precooling unit (or a secondary cooling unit) adapted for precooling the main cooling medium (particularly by a precooling medium (such as electric power providing cooling capacity, a freely moving gas stream transporting cooling capacity, a cold body precooled in a refrigerator and storing thermal energy, etc.)) before supply of the (precooled) main cooling medium to the catheter, wherein the main cooling unit comprises a cooling loop (which may be an open loop or a closed loop, and which may also be denoted as a cooling pathway) through which a fluid is guidable as the main cooling medium, and wherein the precooling unit is free of a cooling loop through which a fluid is guidable.

According to another exemplary embodiment of the invention, a cryosurgery system is provided, the cryosurgery system comprising a catheter and a cooling device having the above mentioned features for cooling the catheter.

According to still another exemplary embodiment of the invention, a method of cooling a catheter is provided, the method comprising supplying the catheter with a main cooling medium, precooling the main cooling medium before supplying the main cooling medium to the catheter, guiding a fluid as the main cooling medium through a cooling loop, and performing the precooling without guiding a fluid through a cooling loop.

In the context of the application, the term "cooling device" may particularly denote an apparatus which is adapted to provide a cooling effect, i.e. to carry off heat in order to reduce the temperature of a destination body such as a catheter.

The term "main cooling unit" may be denoted as a portion of the cooling device which provides actual thermal contact to the catheter to thereby directly cool the catheter, preferably using a loop along which a refrigerant is transported (for instance pumped, or transported by the internal pressure of the refrigerant) to provide for a heat exchange with the catheter to be cooled, thereby cooling the catheter.

The term "precooling unit" may particularly denote an additional component of the cooling device which is capable of being brought into thermal coupling or thermal interaction with the main cooling unit to precool a cooling medium such as a refrigerant of the main cooling unit before an actual thermal coupling between the precooled refrigerant and the catheter is performed.

The term "cooling loop" may particularly denote a cooling pathway, a conduit, channel, or capillary through which a fluid is transportable, for instance under the influence of a pump or by an intrinsic (or own) pressure of the fluid. Such a cooling loop may be a closed loop allowing for a (for instance continuous) circulation of the fluid. Alternatively, the cooling loop may be an open loop which may have a source (such as a fluid container or reservoir) and may have a destination (such as a waste or collector). A characteristic of the cooling loop may be that the cooling loop defines a fluidic path along which the fluid is transported, i.e. limits the degree of freedom of the motion of the fluid.

The term "fluid" may particularly denote any liquid or gaseous substance, or a combination thereof (for instance a two-phase mixture). However, the fluid may also be a liquid having solid components, such as a suspension. Such a fluid may be a refrigerant.

The term "not recover used precooling medium" may particularly denote that the cooling device may be free of any feedback or recovering system for recycling or recovering a precooling medium after the precooling procedure. Thus, no recycling of the precooling medium is performed, or the precooling medium is employed for a single use. The precooling unit may be free of a feedback loop for recovering the used precooling medium. Thus, an open precooling system may be provided in which the precooling medium may dissipate after use. In other words, a non-cyclic precooling architecture may be implemented in which for each precooling sequence, another precooling medium may be used. No regain of the precooling medium may be performed. In accordance with this, the precooling medium may be electric current for operating a thermoelectric cooler, thermal energy stored in a precooled body, a fluidic stream cooling a thermally coupled member, or the like. According to an exemplary embodiment, the precooling medium is consumed during the precooling procedure.

The term "catheter" may particularly denote a tube having a tip that can be inserted into a body cavity, duct or vessel. Catheters may thereby allow access by surgical instruments. A catheter may be a thin, flexible tube. In other embodiments, a catheter may be a stiff tube. Its diameter may vary particularly between 0.3 mm and 10 mm. In an embodiment, a cryoprobe may also be denoted as a catheter.

The cooling device may comprise a control unit adapted for controlling the main cooling unit and/or the precooling unit to perform a predetermined cooling procedure. Such a control unit may be a CPU (central processing unit) or a microprocessor which may be programmed in such a manner that a specific cooling sequence may be carried out. Such a control unit may be a feed forward control unit or may include a feedback, then operating as a regulating unit. The control unit may control operation of valves, pumps, sensors, etc. The control unit may supply electric control signals to the various units, for example to a thermoelectric unit serving as a precooling unit.

The control unit may be adapted for activating the precooling unit before activating a supply of the main cooling medium by the main cooling unit to the catheter. In other words, the circulation of the refrigerant of the main cooling unit may be delayed until a precooling unit has precooled the system to a desired temperature. This may allow to use, after switching the main cooling unit into an active state, the entire system from the first moment onwards in a very efficient manner so that an initial cooling enthalpy can be provided. In other words, only when the precooling unit has been brought to an operation state in which the precooling service can be provided, the main cooling unit is switched on.

According to an exemplary embodiment of the invention, a cooling device for a cryosurgical catheter is provided which cools the catheter for interaction with surrounding tissue (for instance heart tissue of a patient) by a main cooling unit which, before being brought in thermal interaction with the catheter, may be made subject of a precooling procedure of the main cooling medium by a thermal contact with a precooling medium. The precooling medium can be provided by a loop free system or an open system which does not recover the precooling medium after the precooling procedure, thereby preventing high costs and constructional effort for recovering such a precooling medium or for guiding a fluid through a loop of the precooling mechanism. Therefore, size, cost and convenience of operating the cooling device according to an exemplary embodiment of the invention may be significantly reduced. Hence, a simplified and less complex system may be provided which is capable of efficiently precooling a main cooling medium of a main cooling unit without involving a high degree of complexity. Particularly, efficient thermoelectric precooling may be made possible for cryosurgery. More particularly, methods and devices are provided for precooling a refrigerant in cryosurgery and still more particularly for catheter based cyroablation of cardiac arrhythmias. Thus, without a fluid propagating or circulating through a precooling system in a controlled manner, an efficient precooling may be ensured. Particularly, exactly one, i.e. a single, cooling loop or a single fluid pathway may be foreseen in the entire cooling device, namely a cooling loop of the main cooling unit. According to an embodiment, a single-loop cooling device having a precooling mechanism may be provided.

Next, further exemplary embodiments of the cooling device will be explained. However, these embodiments also apply to the cryosurgery system and to the method of cooling a catheter.

As an alternative to an embodiment in which the precooling medium is free of a cooling loop or a cooling pathway, an alternative embodiment comprises a precooling unit which comprises a cooling loop or cooling pathway through which a fluid is guidable as a precooling medium. In a heat exchanger, the precooling medium may precool a body of the heat exchanger so that the main cooling medium can be cooled down to a desired temperature. It is also possible that the main cooling medium is brought in heat exchange with the precooling medium directly. In an embodiment, it is possible that the main cooling medium and the precooling medium have the same composition, for instance both comprise nitrous oxide.

The control unit may be adapted for enabling activation of the main cooling unit by a user only when a temperature of the heat exchanger achieved by the precooling has fallen below a predefined value (which may be, for instance, +5° C.). In practice, a surgeon operating the device may start a cryoablation procedure, for instance by pressing a "start" button. However, the system may be configured for rejecting such a user-defined start when determining that the precooling temperature is not yet sufficiently low. By taking this measure, it may be safely prevented that the surgery is started too early. It is possible to promote a fast arrival at a desired temperature required for stating the surgery, as will be explained below in more detail.

The control unit may be adapted for supplying the main cooling medium with a variable coolant flow rate, particularly a coolant flow rate which is variable over time. Hence, it is possible that the flow rate of the coolant is used as a design parameter or a control parameter for adjusting a desired operation point of the device.

The control unit may be adapted for supplying the main cooling medium with a variable main cooling power by storage of cooling enthalpy. The control unit may be adapted for storing this cooling enthalpy before activation of the main cooling unit. Storing cooling enthalpy may modulate the flow rate. The term "main cooling power" may denote a cooling power of the main cooling unit, and may be a value in Watt. For instance, a high flow of the main cooling medium and/or a low temperature of the cooling medium may result in an increase of the cooling power.

Particularly, the control unit may be adapted for supplying the main cooling medium in an early stage after activation (for instance directly after activation) with a first coolant flow rate, which is larger than a second coolant flow rate supplied at a later stage after activation. Furthermore, the temperature of the main cooling medium in the high pressure supply line at the connection with the catheter may be lower in an early state compared to a later stage. In such an embodiment, a cooling boost at a beginning may be followed by a time period in which the coolant flow rate is reduced. It is possible but not necessary that the flow rate of the cooling medium changes with time, for instance is larger in an early state compared to a later stage.

Particularly, the control unit may be adapted for supplying the catheter after activation with a first value of the main cooling power which is larger than a second value of the main cooling power supplied at a later stage after activation.

The control unit may be adapted for controlling a current flow through the thermoelectric cooling element to thereby modify a precooling power over time. Hence, it is possible that the electric current for driving the Peltier element is used as a design parameter or a control parameter for adjusting a desired operation point of the device.

The control unit may be adapted for switching a current supplied to the thermoelectric cooling element between two values. In one embodiment, the system may switch between a "low" current value and a "high" current value which allows for a simple system. In another embodiment, the system may switch between more than two different discrete values maintaining simplicity while refining the accuracy of controlling or regulating.

Particularly, the control unit may be adapted for continuously regulating a current supplied to the thermoelectric cooling element. In such an embodiment, a stepless control or regulation of the current is possible. This may allow further refining of the controllability of the system.

The cooling device may be adapted to be operable in a manner that at least a part of cooling enthalpy provided by the precooling unit during the precooling is stored in a condensation of the main cooling medium before starting the main cooling. Hence, when evaporated main cooling medium is liquefied during the precooling by storing a portion of the cooling power generated during precooling, a very efficient use of the precooling power may be ensured. Liquid main cooling medium which is about to evaporate may thus be kept in the liquid state. This may allow for an efficient conditioning of the main cooling medium.

A difference between temperatures of the heat exchanger at an end of a main cooling sequence and a start of the main cooling sequence may be greater than 5° C., particularly greater than 10° C. An exemplary initial temperature is +5° C.

The cooling unit may comprise a cooling loop (which may be an open loop having an inlet and an outlet, or which may be a closed loop having a cyclic architecture) adapted for supplying the catheter with a refrigerant, particularly with nitrous oxide ($N_2O$). Such a refrigerant or coolant may be a compound used in a cooling procedure or cycle that undergoes a phase change from liquid to gas, and optionally back. Such a cooling loop may comprise a tubular line having a lumen through which the refrigerant may be transported, for instance may be pumped. A hollow wall of the cooling loop may be made of a material which properly thermally isolates the refrigerant during circulation along the cooling loop. As an alternative to nitrous oxide, it is also possible to use other cooling agents, for instance liquid nitrogen, liquid helium, liquid oxygen, liquid air, argon, or the like.

The precooling unit may comprise a thermoelectric cooling element, particularly a Peltier element. The thermoelectric effect used in such an embodiment is based on the conversion between electrical energy and thermal energy. Particularly, when applying an electric current to a Peltier element, a specific portion of the Peltier element may be cooled, whereas another portion of the Peltier element may be heated. By bringing the cooled portion of the Peltier element in thermal contact with the refrigerant of the main cooling unit, a precooling of the refrigerant of the main cooling unit may be obtained. Thermoelectric cooling may use the Peltier effect to create a heat flux between the junction of two different types of materials (particularly metals). A Peltier cooler or thermoelectric heat pump may be a solid-state active heat pump which transfers heat from one side of the device to the other side against the temperature gradient (from cold to hot), with consumption of the electrical energy. In the case of a Peltier element, the cooling medium of the precooling unit is electric current. According to an exemplary embodiment, this current is not recovered after use, so that it is used only once.

The precooling unit may comprise a frozen body, particularly a frozen body of a material being liquid at 20° C. (such as water), more particularly an ice body (of water, $H_2O$). Therefore, a material brought to a low temperature may also be used as the precooling medium when being brought in interaction with the refrigerant of the main cooling unit. When the cooling device is operated in a lab or in a hospital at room temperature of, for instance 20° C., the frozen body brought to a lower temperature (for instance to 0° C.) may provide cooling energy to the refrigerant of the main cooling unit. For example, ice cubes may be used which can be placed to simply surround a line (for example to circumferentially contact the line) through which the refrigerant of the main cooling unit passes. With very low effort, this may allow for a very efficient cooling in an open system in which the cooling medium, namely the cooling energy introduced into the solidified body, is not recovered. When using aqueous ice cubes, the high thermal capacity of the cheap material water may be used, and the latent energy of melting of water may be useful as well.

Additionally or alternatively, the precooling unit may comprise a solid body (for instance being solid at room temperature of 20° C.) cooled below 20° C. (particularly cooled below 0° C., more particularly cooled below −20° C.), more particularly a metallic body, still more particularly a cold copper body. For example, a body having a sufficiently high heat capacity and a sufficiently good thermal conductivity may be used as such a precooling medium, for instance a copper block which may be brought in thermal contact with the refrigerant of the main cooling unit for precooling purposes. Also in this case, the cooling energy stored in the precooled solid body may be used for precooling the main cooling medium, without recovering the consumed cooling energy after use.

The frozen or solid body may be precooled in a refrigerator or the like. It is also possible that the frozen body or solid body being precooled is stored, also during use, within a Dewar or some kind of thermos bottle.

The precooling medium may comprise a coolant spray, for instance ice spray. Therefore, by spraying such a cooling fluid onto the main cooling unit, particularly onto a properly thermal conductive portion of a line of the main cooling unit, cooling power may be provided in an efficiently and dosable manner, thereby allowing a further refined cooling procedure. Again, also in an embodiment involving a coolant spray, no recovery or recycling of the ice spray material forming the precooling medium may be performed.

The precooling unit may comprise a ventilator adapted for providing a ventilation fluid stream (for instance gaseous and/or liquid) adapted for precooling the main cooling medium. The ventilation stream of a suitable fluid, for instance air, may or may not be precooled. Thus, by thermal convection, if desired combined with thermal conduction, precooling the main cooling medium may be achieved, wherein the precooling medium in the form of a ventilation stream is not recovered.

The precooling unit may comprise a refrigerator adapted for precooling the precooling medium. A refrigerator may be a cooling appliance comprising a thermally insulated compartment and a mechanism to transfer heat from it to the external environment, cooling the contents to a temperature below ambient. Such a refrigerator may be a device having a cooled interior in which the precooling unit or a portion thereof (for instance only the precooling medium) may be stored before use of the cooling device in the context of cryosurgery. Then, the cooled precooling unit (or the portion thereof) may be taken out of the refrigerator and may be brought in thermal contact with the refrigerant of the main cooling unit outside of the refrigerator.

The cooling device may comprise a heat exchanger arranged to provide a thermal coupling between the main cooling unit and the precooling unit, or more precisely between components thereof. The heat exchanger may be a device which provides a proper thermal coupling between the main cooling medium (which may also be denoted as a primary cooling medium) and the precooling medium (which may also be denoted as the secondary cooling medium). Such a heat exchanger may be a device which transfers heat through a conducting wall from one fluid to another. In such a device, heat may be transferred from a medium (such as an electric current, or stored cooling energy) to another medium (such as a fluid) a fluid, wherein the two media may be physically separated (for instance by metal tubing). A heat exchanger may be built for efficient transfer from one medium to another, wherein the fluids may be separated by a solid wall so that they never mix. Alternatively, the media may be directly contacted.

The cooling device may further comprise a heat sink, wherein the precooling unit may be arranged between the heat sink and the heat exchanger. In certain embodiments, the secondary cooling unit not only cools the refrigerant of the main cooling unit, but also generates waste heat (in other embodiments, such as a metal body precooled in a refrigerator, such waste heat is not produced in the cooling device, but at the refrigerator). In such a scenario, the heat sink may be located to properly lead away the waste heat from the environment of the cooling device, thereby preventing cooling losses. Cooling fins or cooling webs may be used as examples for such a heat sink, or a precooled body such as a copper body which has been stored in a refrigerator beforehand.

Thus, the heat sink may be an environment or object that absorbs dissipated heat from another object via a thermal contact.

The precooling unit (for instance when comprising a Peltier element) may comprise a first surface (which may be denoted as a warm side) having a temperature above a temperature of a second surface (which may be denoted as a cold side). Particularly, a warm side of the precooling unit may be thermally coupled to the heat sink and a cold side of the precooling unit may be thermally coupled to the heat exchanger. Therefore, cooling energy may be transferred from the precooling unit via the heat exchanger to the refrigerant of the main cooling unit, whereas waste heat from the precooling unit may be transported away from the cooling device by the heat sink.

The heat sink may be adapted to carry away heat from the precooling unit by at least one mechanism of the group consisting of a heat conduction mechanism, a heat convection mechanism, a liquid cooling mechanism, and a heat pipe mechanism. Heat conduction may be denoted as a heat transfer by means of molecular agitation within a material without any motion of the material as a whole. Convection may be denoted as heat transfer by mass motion of a fluid such as air or water when the fluid is caused to move. A liquid cooling medium which may be used for the heat sink may be a circulating fluid such as water or any other cooling agent which may be brought in thermal contact with the heat sink to transport heat away from the cooling device. A heat pipe may also be used which may be denoted as a heat transfer mechanism that can transport large quantities of heat with a very small difference in temperature between a hot and a cold interface. Inside a heat pipe, at a hot interface a fluid may turn to vapor and the gas naturally flows and condenses on the cold interface. The liquid falls or is moved by capillary reaction back to the hot interface to evaporate again and repeat the cycle.

The heat sink may comprise a solid body cooled below 20° C., more particularly a metallic body, still more particularly a copper body. Thus, the heat sink may be configured in a similar manner as the precooling unit in a specific embodiment.

A thermal insulator may be provided surrounding at least a part of the heat exchanger. By taking this measure, thermal energy losses with regard to the environment may be securely prevented.

The cooling device may comprise a pressure generator adapted for supplying pressure for pumping the main cooling medium, such as a refrigerant (for example nitrous oxide), along the cooling device. At least a part of the pressure generator, particularly a pressure reducer (if desired also a pressure sensor), may be accommodated within the thermal insulator. The thermal insulator may enclose at least a portion or the entire part of the pressuring system which shall be thermally insulated against an environment.

The control unit may be adapted for controlling a value of an electric supply signal (such as an electric current or an electric voltage) flowing through the thermoelectric cooling element of the precooling unit in accordance with a value of a temperature sensed in a portion of the cooling loop downstream (in a flowing direction of the refrigerant) the catheter. For example, the control unit may measure a temperature of the refrigerant of the main cooling unit after thermal exchange with the catheter. Based on this temperature value, the value of the electric current driving the Peltier element may be controlled/regulated, for instance may be increased or decreased, to thereby regulate the temperature and the cooling performance at the position of the catheter to a desired value.

Particularly, the control unit may be adapted for controlling a value of a current flowing through the thermoelectric cooling element of the precooling unit based on a value of a temperature sensed in the catheter at a position downstream of a boiling chamber of the catheter. A temperature downstream a boiling chamber of the catheter, i.e. after the refrigerant has been evaporated, is a very sensitive position in the fluidic path regarding current control. With such a location of a temperature sensor, the regulation may be performed in an operation state close to the sharp bend of the curve on the low right hand side of FIG. 4, where the curve has a high value of the derivation, i.e. a sufficiently large gradient. In some embodiments, the boiling chamber may be oblong (for instance may have a length of 10 cm and a diameter of 2 mm).

It is noted that an independent aspect of the invention is directed to the implementation of a temperature sensor adapted for sensing a temperature in the catheter at a position downstream of a boiling chamber of the catheter, and to use the measured temperature as a control criteria for controlling the performance of the cooling system. Particularly, this aspect may be implemented independently of the provision of a precooling unit. Thus, such a temperature-measurement based control of the cooling mechanism may be implemented as well in a scenario in which no precooling unit is foreseen.

A valve comprising bypass line (i.e. a bypass line in which a valve is foreseen) may be provided allowing to selectively (i.e. under control of a user or a control unit) connect a first position of the cooling loop upstream of the precooling unit (i.e. at a position at which a flowing refrigerant of the main cooling unit has not yet been brought in thermal contact with the precooling unit) with a second position of the cooling loop downstream of the catheter (i.e. at a position at which a flowing precooled refrigerant of the main cooling unit has already been brought in thermal contact with the catheter) so that after terminating the supply of the refrigerant to the catheter, the valve is openable (for instance under control of the control unit) to bypass (or short circuit) the first position and the second position. For example, after having finished a main cooling procedure in the context of a cryosurgery operation, some refrigerant may remain within the supply line of the main cooling unit upstream of the catheter. By activating the bypass line, remaining refrigerant may flow through the bypass line to instantaneously terminate the cooling procedure. In another context, U.S. Pat. No. 6,471,694 discloses a bypass line as such. Bypass lines as the one disclosed in U.S. Pat. No. 6,471,694 can be implemented according to exemplary embodiments of the present invention, particularly for cooling a precooler.

The valve comprising bypass line may comprise a coupling portion which is guided through the heat exchanger. For example, after having finished a main cooling procedure in the context of a cryosurgery operation, some refrigerant may remain within the supply line of the main cooling unit upstream of the catheter. Instead of wasting this remaining refrigerant, it may be efficiently used by the described bypass operation, since the refrigerant may be guided to the heat exchanger, thereby efficiently precooling the device for the next main cooling sequence in a multiple stage procedure. In other words, the cooling capacity of the remaining refrigerant may be used for contributing to the cooling enthalpy stored for the efficient cooling in the next sequence.

In this context, particularly when the coupling portion comprises an expansion element for expansion (particularly for an approximately isenthalpic expansion) of a medium expanding from the coupling portion into the expansion element, the refrigerant transported through the bypass line can be used for precooling the precooling unit after the main cooling procedure, thereby providing a proper preparation of the cooling device for the next cooling sequence.

The precooling unit may be adapted to not recover the used precooling medium after precooling the main cooling medium. In other words, it is possible that the precooling medium (for instance an electric current in case of a Peltier element, stored cooling energy in case of a precooled metal block, cooling spray, a precooled gas stream of a fan) is not recycled after use. This may allow for a simple construction, since no closed recovery cycle is needed in such an embodiment.

The precooling unit may be adapted for precooling the main cooling medium by a precooling medium before supply of the main cooling medium to the catheter. Thus, before operating on the catheter, the main cooling medium is treated with the precooling mechanism to precool the main cooling medium before expanding in a boiling chamber of the catheter.

The cooling loop of the main cooling unit may be the only cooling loop of the cooling device. Thus, a cooling loop portion of the entire cooling device may have exactly one cooling loop, namely the cooling loop of the main cooling system. This promotes a simple and cost efficient construction of the cooling device.

The cooling loop may comprise one of the group consisting of an open cooling loop and a closed cooling loop. An open cooling loop architecture may take main cooling fluid from a reservoir in a liquid phase, may conduct the liquid through a tube into the catheter, may evaporate the liquid to transfer it into a gaseous phase in a boiling chamber of the catheter thereby cooling the catheter, and may guide the evaporated refrigerant into a waste. A closed cooling loop architecture may take main cooling fluid from a reservoir in a liquid phase, may conduct the liquid through a tube into the catheter, may evaporate the liquid to transfer it into a gaseous phase in a boiling chamber of the catheter thereby cooling the catheter, and may guide the evaporated refrigerant for re-liquidation, so that a circulation of the material without beginning and end is effected.

The heat exchanger may be made of a material having a thermal capacity in a range between essentially 1.5 J/K and essentially 1500 J/K, particularly in a range between essentially 15 J/K and essentially 150 J/K, more particularly of essentially 50 J/K. By carefully designing the value of the heat capacity of the heat exchanger, the cooling enthalpy may be adjusted appropriately. Design parameters of the heat exchanger are the material (for instance copper or any other material having a sufficient heat capacity and thermal conductivity), the mass, the shape (for instance, the heat exchanger may be shaped with planar surfaces to thereby promote the coupling properties to adjacent components, may be shaped in a cuboid manner, and may have internal bores (for instance by milling) to obtain a large effective inner surface) and the temperature of operation. Before starting the main cooling sequence, the heat exchanger will be cooled to a defined temperature. When the main cooling cycle is started the temperature in the heat exchanger will rise as the main cooling medium delivers heat into the heat capacity of the heat exchanger. The temperature difference between the initiation and termination of the main cooling sequence and the heat capacity define the cooling enthalpy in the context of the invention.

Precooling may be performed by cooling a cooling agent in a refrigerator (for instance in a bottle), that is to say by cooling it below room temperature (for example 20° C., atmospheric pressure). This precooled cooling agent may then be brought in thermal contact with the refrigerant of the main supply unit, thereby allowing for an efficient cooling.

It is also possible to store a part of the fittings, mountings and/or controlling instruments of the cooling device in a refrigerator and to mount these portions before use of the main cooling unit. Also this may allow for an efficient precooling.

Cooling (for instance using nitrous oxide as a cooling agent) may be based on the effect of approximately isenthalpic expansion (Joule-Thomson-Effect), namely a transfer from a liquid to a gaseous phase accompanied by the generation of cooling energy under specific thermodynamic conditions.

It may be advantageous that the cooling power varies with time during an ablation procedure. At the beginning, the cooling power may be larger that later, when an ice layer which may be formed at the catheter tip acts as a thermal resistance or barrier. Thus, the initial cooling power may be larger than a later cooling power. In other words, precooling may be adjusted to be more efficient at the beginning than later (for instance using a precooled body which warms during the precooling, or using a Peltier element which is driven with a current amplitude decreasing with time).

In an embodiment, a pressure reducer is provided for reducing the pressure at the catheter to properly set a working condition of the cooling device. It may be advantageous to precool the system to a value so that the refrigerant evaporates exactly at the catheter tip.

Upon determining that the present precooling and/or cooling power is too large, it may be possible to invert the polarity of the driving current of the Peltier element of the precooling unit. This may result in a conversion of the previous cold side of the Peltier element into a warm side and of the previous warm side of the Peltier element into a cold side, allowing for a flexible and efficient heating, until the system is brought back into a desired temperature/cooling state. Then, the polarity can be inverted again to bring the system back into a cooling operation.

BRIEF DESCRIPTION OF THE FIGURES

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

FIG. 1A to FIG. 1C illustrates a computer simulation of ice formation in cryosurgery comparing three modes of cooling power delivery.

FIG. 3A to FIG. 3D illustrate the storage of a cooling enthalpy in a heat exchanger by operating a Peltier element at a constant current.

FIG. 10 illustrates the storage of a cooling enthalpy in a heat exchanger by operating a Peltier element with a switched current.

The illustration in the drawing is schematically. In different drawings, similar or identical elements are provided with the same reference signs.

DETAILED DESCRIPTION

Figure 2:
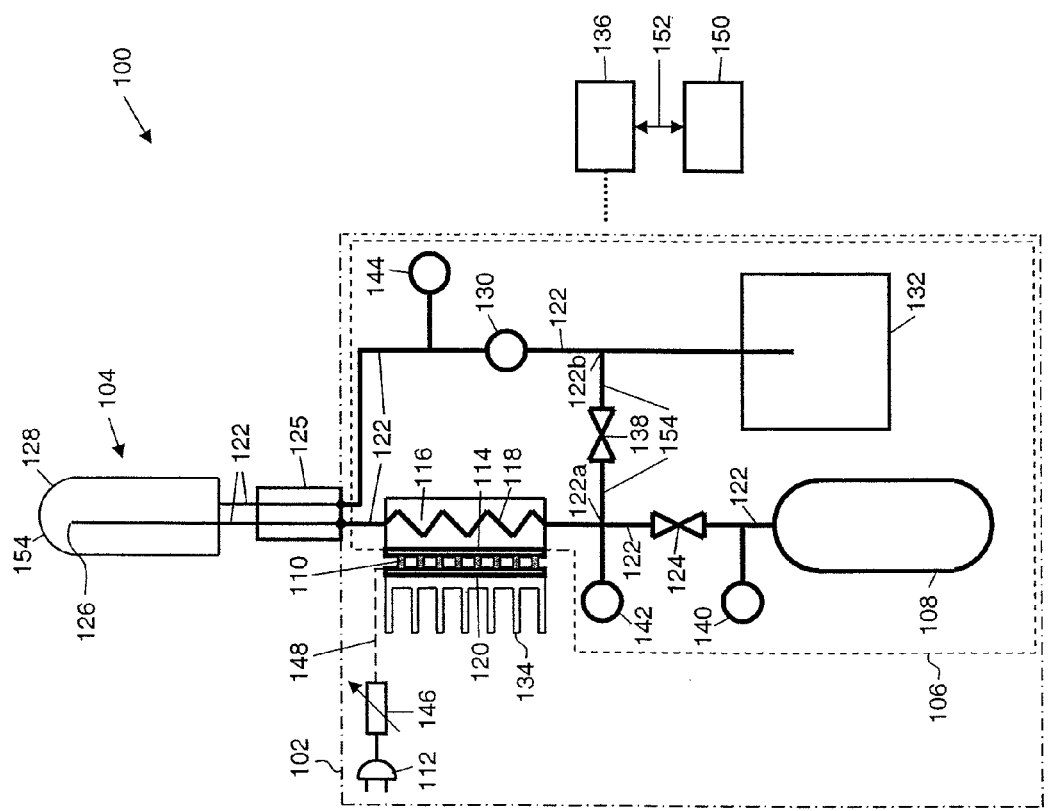
FIG. 2 illustrates a cryosurgery system according to an exemplary embodiment of the invention.

Without wishing to be bound to a specific theory, it is presently believed by the present inventors that phenomena described in the following might contribute to advantageous technical effects achieved by exemplary embodiments of the invention.

(Bio)physical parameters affecting the formation of ice during cryosurgery can be studied by means of computer simulation. In FIG. 1, results of a computer model of the formation of ice ball (half sphere) in myocardial tissue are shown. The model is based on the Pennes bioheat equation and the effective heat capacity model for freezing tissue.

FIG. 1A illustrates a diagram 100 having an abscissa 102 along which a time is plotted. Along an ordinate 104 of the diagram 100, a normalized power is plotted.

FIG. 1B illustrates a diagram 130 having an abscissa 102 along which a time is plotted. Along an ordinate 134 of the diagram 130, a temperature is plotted.

FIG. 1C illustrates a diagram 160 having an abscissa 102 along which a time is plotted. Along an ordinate 164 of the diagram 160, a radius of an ice ball is plotted.

The three panels 100, 130, 160 depict cooling power, temperature in an exemplarily observation point in the tissue (0.75 mm from the catheter tip) and the radius of the ice ball for three simulations with varying cooling power.

An efficient delivery of cooling power was simulated by assuming that the heat transfer from the refrigerant to the catheter tip is governed by the product of the heat transfer coefficient of the refrigerant with the inner surface of the tip and the difference of the boiling chamber temperature (set to −90° C. for the given example) and the tip temperature (initial value is the body temperature). The simulated main cooling power 11a contains an initial peak, as for the large initial temperature difference an increased heat flow is obtained. As the catheter tip cools down the delivered cooling power decreases to a constant value $p_\infty$ (compare reference numeral 11b). The cooling power $p_\infty$ defines the upper limit for the heat transfer in the steady state when the ice ball has been grown to its maximal extension (4.5 mm in this example). In the early phase of freezing a higher cooling power can be delivered which contributes to fast growing of ice (compare reference numeral 13a) and to rapid cooling of the tissue (compare reference numeral 12a). The present inventors have recognized that this initial peak of cooling power can only be obtained by proper technical means which ensure that proper quantity of liquid refrigerant is delivered when freezing is started.

In computer simulations often a constant delivery of cooling power is assumed and some devices in cryosurgery tend to deliver a constant coolant flow at an essentially constant precool temperature. For comparison the temperature 12b and ice ball size 13b are plotted for a constant cooling power $p_\infty$ (11b) modeled by a Neumann boundary condition. Initially there is a remarkably slower decay of the temperature which is also reflected by slower growing of the ice ball. However, in the steady state both simulations yield the same lesion size and identical temperatures in the entire domain. If a higher cooling power (for instance twice the power $p_\infty$) is delivered to the catheter this will not change the final size of the ice ball as the maximal steady state heat transfer is limited by the thermal resistance of the catheter and the boiling chamber temperature. Thus, in the steady state any additional cooling power provided by the coolant can not be used in the boiling chamber but will chill the catheter in the back stream. This can lead to undesired freezing of the device in a vessel or a sheath.

Immediately before freezing is started, the refrigerant supply lines outside the body are approximately at room temperature and approximately at body temperature inside the body. The boiling temperature of the refrigerant for the given pressure in the supply line is at the room temperature or below. Thus, when starting to freeze the refrigerant boils out in the supply lines cooling them to the boiling temperature of the refrigerant. The initial cooling power in the tip will be small and increase only with some decay as shown exemplarily by the graph 11c. In this case an even more pronounced delay of ice ball formation 13c and temperature decrease 12c is obtained. However, the final size of the ice ball and the steady temperature profile is the same as for the two examples above.

From a clinical point of view, fast initial cooling and a fast formation of the ice layer is desirable. First, fast freezing ensures that the catheter is fixed in the location where the ablation has been started and avoids catheter displacement. Second, high cooling rates promote the formation of intracellular ice which contributes to the lethal effect of cryoablation. Third, the time needed for obtaining a steady state is reduced leading to shorter freezing cycles.

From FIG. 1A to FIG. 1C, two observations can be made. First, the area between graph 11a (efficient cooling power delivery) and graph 11b (constant cooling power delivery) has a finite value corresponding to an additional "main cooling enthalpy" supplied. Second, for cooling the supply lines to their operation temperature a certain amount of heat has to be withdrawn from these lines which is mainly determined by the heat capacity of the lines and the difference of line temperature and boiling temperature. Also here, an additional "cooling enthalpy" has to be supplied for fast chilling of the supply lines to the operating temperature.

In embodiments of the invention, proper means are described for delivering an initial cooling enthalpy which triggers the fast freezing of the catheter tip. In one exemplary embodiment of the invention a precooling enthalpy is stored in the heat capacity of a heat exchanger. In another embodiment a high initial supply pressure drives an increased initial coolant flow.

In the following, referring to FIG. 2, a cryoablation system 100 according to an exemplary embodiment of the invention will be explained.

The cryoablation system 100 comprises a cooling device 102 for cooling an ablation catheter 104 for ablating heart tissue of a human being.

The cooling device 102 comprises a main cooling unit 106 adapted for supplying the catheter 104 with a main cooling medium, namely (precooled) nitrous oxide ($N_2O$) from a main cooling medium reservoir 108. Preferably, the refrigerant is supplied in its liquid phase for example by using an eductor tube (not shown) within the reservoir 108.

Beyond this, a precooling unit 110 is provided in the form of a Peltier element which can be powered by electric current supplied via a connector 112. In other words, by conducting electric current from a main supply (not shown) via the connector 112 to the Peltier element 110, cooling energy is generated in a cold coupling portion 114 of the Peltier element 110 in direct contact with a heat exchanger 116. Thus, by a thermal contact between the cooling energy generated at the surface 114 by the Peltier element 110 and nitrous oxide flowing through a zigzag line 118 within the heat exchanger 116 may allow to precool the nitrous oxide material before the nitrous oxide material is transported to the catheter 104.

Since the electric current used for powering the Peltier element 110 is not recovered or recycled after generation of cooling energy at the cold edge 114 (and a simultaneous generation of heat at an opposed remote edge 120), the precooling unit 110 does not recover the used precooling medium (electric current in the present embodiment) after precooling the main cooling medium, namely the nitrous oxide.

The main cooling unit 106 comprises a cooling loop, namely a hollow supply line 122 extending from the nitrous oxide reservoir 108 via a valve 124 towards the heat exchanger 116, as a portion 118 through the heat exchanger 116, from the heat exchanger 116 via a handle 125 (which may also be denoted as a grip) of the catheter 104 into the catheter 104 to a portion 126 at which the nitrous oxide is evaporated by an approximately isenthalpic expansion, thereby rapidly cooling an outer surface 128 of the catheter 104 via the Joule-Thomson effect. The evaporated nitrous oxide is then guided back via the cooling loop 122, the handle 125, a flowmeter 130 into a waste 132 at which the used refrigerant stored in the container 108 is accumulated.

A cooling fin 134 is provided as a heat sink, wherein the precooling unit 110 is arranged to be sandwiched between the heat sink 134 and the heat exchanger 116. More particularly, a warm side 120 of the precooling unit 110 is thermally coupled to the heating fin 134, whereas a cold side 114 of the precooling unit 110 is thermally coupled to the heat exchanger 116.

A control unit 136 such as a CPU is shown in FIG. 2 as well and is communicatively coupled to the valves 124, 138, the flowmeter 130, a first pressure sensor 140, a second pressure sensor 142, a temperature sensor 144 and a current regulator 146 circuited in a cable 148 connecting the connector 112 with the Peltier element 110. The (unidirectional or bidirectional) communicative coupling of the CPU 136 with the various members is indicated schematically by dotted lines.

Furthermore, the CPU 136 is coupled to an input/output unit 150 allowing a user to bidirectionally communicate with the control unit 136. For example, the input/output unit 150 may comprise input elements such as a keypad, buttons, a joystick, etc. In some embodiments, the system may be operated by a physician by a foot pedal mechanism. While a patient lies on a table, the physician may manually operate the catheter and may control the cooling procedure by operating the pedal with a foot. Furthermore, the input/output unit 150 may comprise a display unit such as an LCD, a TFT, or a cathode ray tube. Via the communicative coupling line 152 bidirectionally connecting the control unit 136 with the input/output unit 150, a user may provide the CPU 136 with control commands or may receive results from the CPU 136.

At a tip 154 (or, more generally, at a freezing portion) of the catheter 104 at which the catheter 104 can be brought in thermal contact with tissue of a human heart which tissue is to be ablated or destroyed, the temperature may be significantly below 0° C. using the precooling and main cooling procedure. As a rule of thumb, ablation may be achieved by cooling the catheter tip below −20° C. for at least one minute or below −40° C. for a shorter time.

It is also possible to implement the Peltier element 110 within the handle 125 of the catheter 104, the handle 125 allowing a physician to operate the catheter 104 manually.

The waste 132 may be a hospital vacuum. It is also possible to accumulate the used refrigerant in the waste 132, to later recover the refrigerant 132.

As an alternative to the embodiment in which the CPU 136 controls the various valves 124, 138, etc., it is also possible that a human operator controls the valves and all other members of the system 100 manually.

A valve 138 comprising bypass line 154 selectively connects a first position 122a of the cooling loop 122 upstream the precooling unit 110 with a second position 122b of the cooling loop 122 downstream the catheter 104 so that after terminating the supply of the refrigerant to the catheter 104 the valve 138 can be opened (manually or under control of the CPU 136) to bypass the first position 122a and the second position 122b.

FIG. 3A to FIG. 3D illustrate in an example how a finite cooling enthalpy is stored in a heat exchanger by a Peltier element operated at a constant current.

FIG. 3A shows the linear relation between cooling power (compare ordinate 302) and temperature difference ΔT (compare abscissa 304) between the cold side and the warm side (which is close to ambient temperature) which is characteristic for a Peltier element operated at a constant current. The steep characteristic curve shown in FIG. 3A indicates that the implementation of a Peltier cooler for precooling is a very powerful selection, since this allows to obtain a large cooling power and large temperature differences between a minimum temperature and a steady state temperature. Hence, the combination of the delayed main cooling (as compared to precooling) with the implementation of a precooling unit free of a cooling loop (particularly with a thermoelectric precooling unit) is particularly advantageous for obtaining efficient cooling.

FIG. 3B shows the precooling power (compare ordinate 312) over time (compare abscissa 314) and FIG. 3C and FIG. 3D show the precooling temperature (compare ordinate 322) and main cooling power (compare ordinate 332) respectively over time.

When precooling is started (point 31 in FIG. 3A and vertical line t31 in FIG. 3B to FIG. 3D) the temperature difference is zero and the heat exchanger is cooled down with an initially maximal precooling power which decreases with time. The main cooling unit is not operating and for a proper thermal isolation of the heat exchanger it is possible to cool it to a minimal temperature (point 32 in FIG. 3A and vertical line t32 in FIG. 3B to FIG. 3D, note that ΔT is negative). With this minimum the net precooling heat flux converges to zero.

After precooling to the desired temperature the main cooling unit is started by opening a valve in the main cooling loop at t32'. The primary refrigerant is delivered at a temperature which is above the temperature of the heat exchanger. Thus, the heat exchanger warms up to an intermediate temperature which is between the initial ambient temperature and the minimal temperature of the heat exchanger. With increasing heat exchanger temperature the net precooling power increases until a steady state intermediate value $Q_{PC3}$ is obtained. The difference between the steady state temperature and the minimal heat exchanger temperature together with the heat capacity of the heat exchanger define the initial precooling enthalpy in this example.

In FIG. 3B the stored precooling enthalpy is indicated by a hatched area. Note that for the following precooling and main cooling sequence the process is repeated starting in or after point 33. Only for the very first cooling cycle the starting point 31 is chosen as the system has to be cooled down from ambient temperature to the temperature range of cyclic operation. Hence, the initial cycle differs from one or more subsequent cooling cycles which may show repeatable cycles of the system after the initial cycle.

In an embodiment, the absolute difference between the minimum temperature and the temperature in the steady state should be at least 5° C., particularly at least 10° C., more particularly at least 15° C. even more particularly at least 20° C.

Due to the low temperature of the heat exchanger at the beginning of the main cooling sequence (t32) the main cooling medium is initially precooled to a lower temperature compared to the steady state. Thus, the main cooling power is initially higher than in the steady state.

In another embodiment, the Peltier element is operated with an initially higher electric current for reaching a lower minimal precool temperature or for reaching the desired temperature faster.

In the followings, some considerations will be described based on which exemplary embodiments of the invention have been developed.

Figure 4:
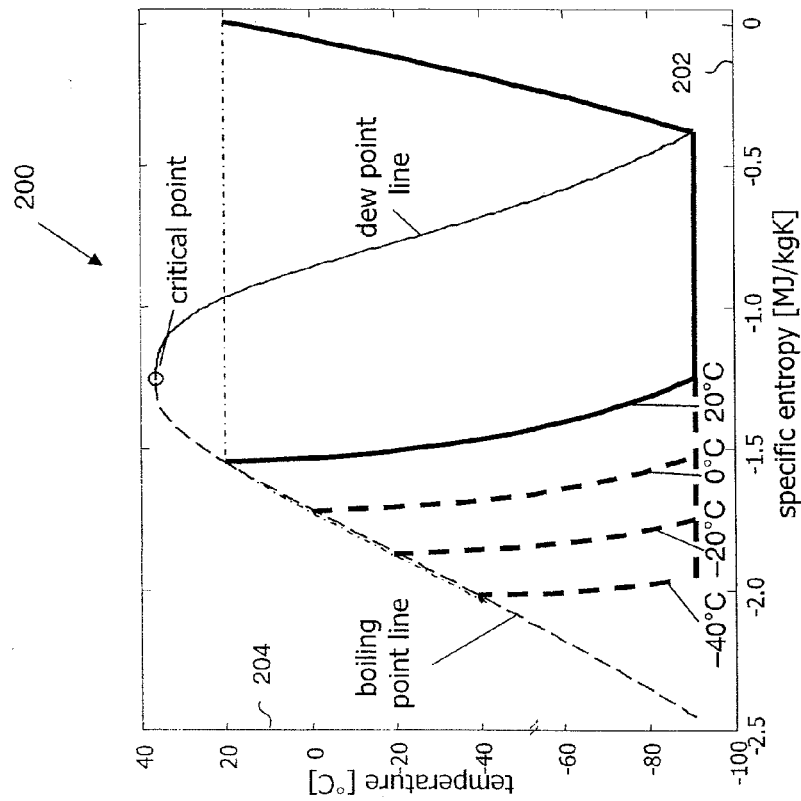

FIG. 4 illustrates a diagram 200 having an abscissa 202 along which a specific entropy is plotted. Along an ordinate 204 of the diagram 200, the temperature is plotted. A similar diagram 300 is plotted in FIG. 5.

Figure 5:
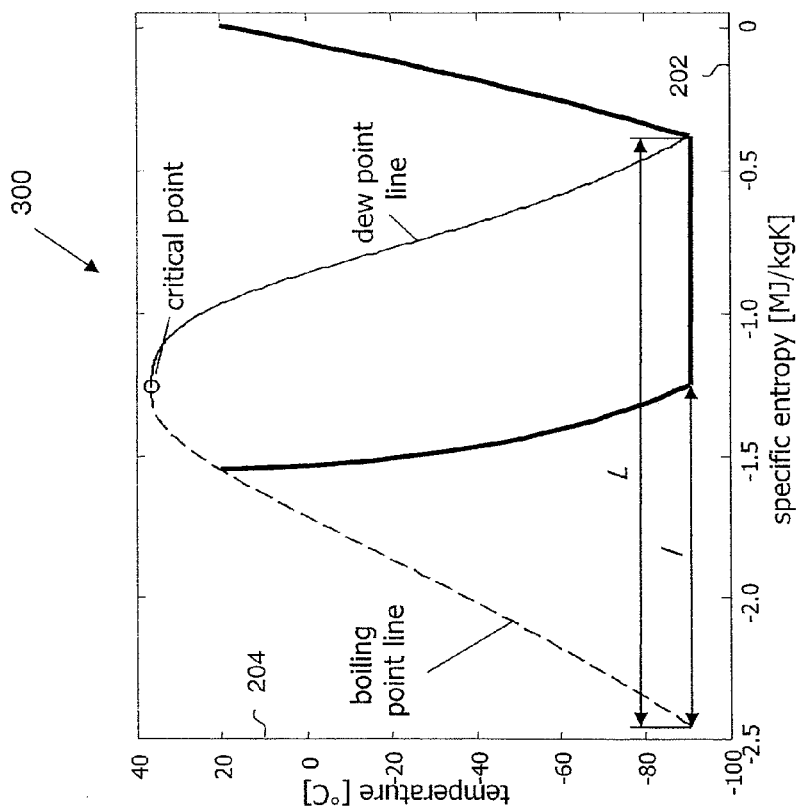
FIG. 4 and FIG. 5 illustrate temperature-entropy-diagrams of nitrous oxide ($N_2O$).

In FIG. 4, FIG. 5, the isenthalpic expansion of a primary refrigerant to a low pressure boiling point is shown for different precool temperatures in the entropy-temperature diagrams 200, 300. The data for nitrous oxide is shown as an example. At lower precool temperatures a larger difference of entropy can be used at the working temperature. The ratio x=1/L yields the relative mass of fluid in the gaseous state obtained after isenthalpic expansion (steam quality). According to exemplary embodiments of the invention, it may be advantageous to have a large amount of liquid at a low steam quality.

Thermoelectric cooling devices realize a heat pump by conduction of electric charge carriers (electrons and defect electrons) at different energy levels in semiconductors (Peltier-effect). In contrast to Joule-Thomson based devices the temperatures obtained by thermoelectric coolers depend strongly on the actual heat flow in the device (almost linear relationship; maximal cooling power at ambient temperature; zero cooling power at lowest temperature).

For single stage devices the lowest achievable temperature is about 70° C. below ambient temperature. Multi stage (cascade) thermoelectric devices can reach lower temperatures. As the precooling power decreases linearly with the temperature difference (hot versus cold side temperature) in the device, a high precooling power is obtained at a relatively small temperature difference.

Ambient conditions and in particular ambient temperature influence the primary refrigerant in the high pressure stream of the control system for cryosurgery. In particular, if the primary refrigerant is kept in this liquid phase in the high pressure stream the ambient temperature defines the pressure in the high pressure stream. The high pressure is the pressure of vaporization at the ambient temperature for the used fluid. For example, if nitrous oxide is used as a primary refrigerant the vapor pressure is about 63 bar at +30° C. and about 45 bar at +15° C. (see FIG. 4).

Figure 6:
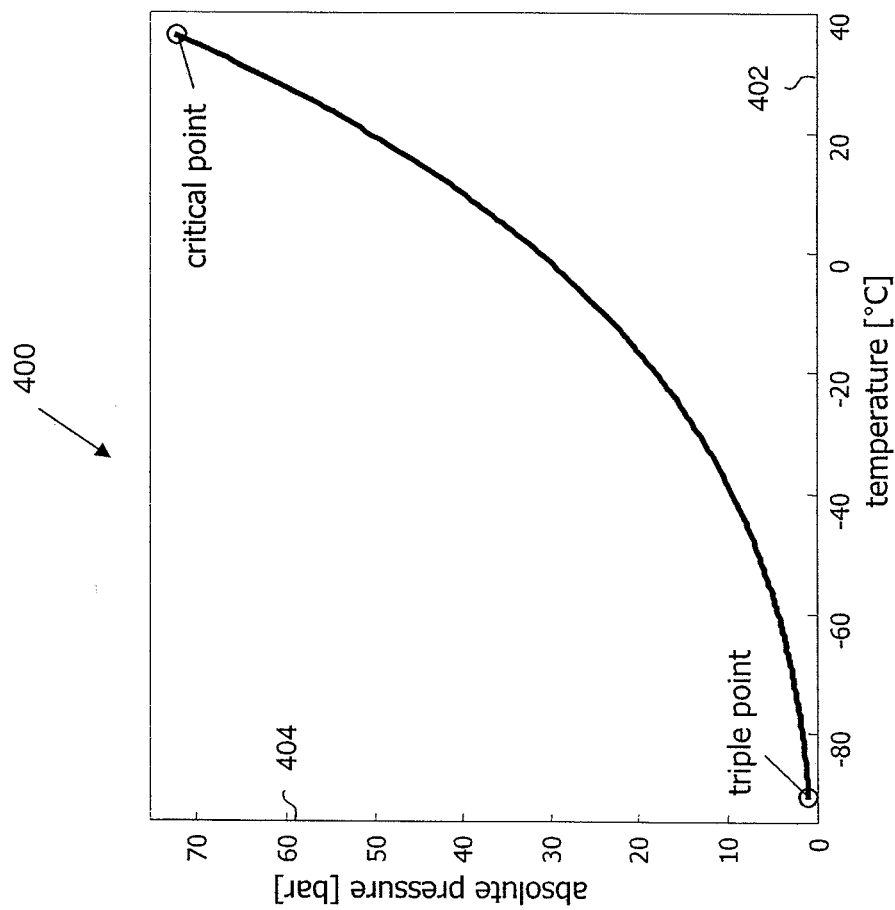
FIG. 6 illustrates vapor pressure as a function of temperature for nitrous oxide ($N_2O$).

FIG. 6 illustrates a diagram 400 having an abscissa 402 along which the temperature is plotted. Along an ordinate 404, a vapor pressure is plotted. In the diagram 400 of FIG. 6 the vapor pressure is plotted as a function of the temperature for nitrous oxide ($N_2O$).

In view of the above considerations, the present inventors have recognized that it would be desirable to reduce the high pressure to a constant controlled smaller value for safety issues and for operating the system at a well defined pressure. However, pressure reduction leads to an—at least partial— vaporization of the primary refrigerant in the high pressure duct and in turn to a loss of cooling power without applying proper means for avoiding vaporization.

In the following, a further exemplary embodiment of a cryocatheter system 500 will be explained referring to FIG. 7.

In addition to the components already mentioned referring to FIG. 2, the cryosurgery apparatus 500 particularly further comprises a temperature sensor 541 in the heat exchanger 116, a temperature sensor 540 in the catheter 104, a temperature sensor 542 downstream of the catheter 104, a pressure sensor 522 and a connection 502 to an atmosphere or the vacuum. Further, a zigzag line 523a of the supply line 122 within the heat exchanger 116 is shown which promotes the thermal exchange within the line 122 with the precooling unit 110.

Figure 7:
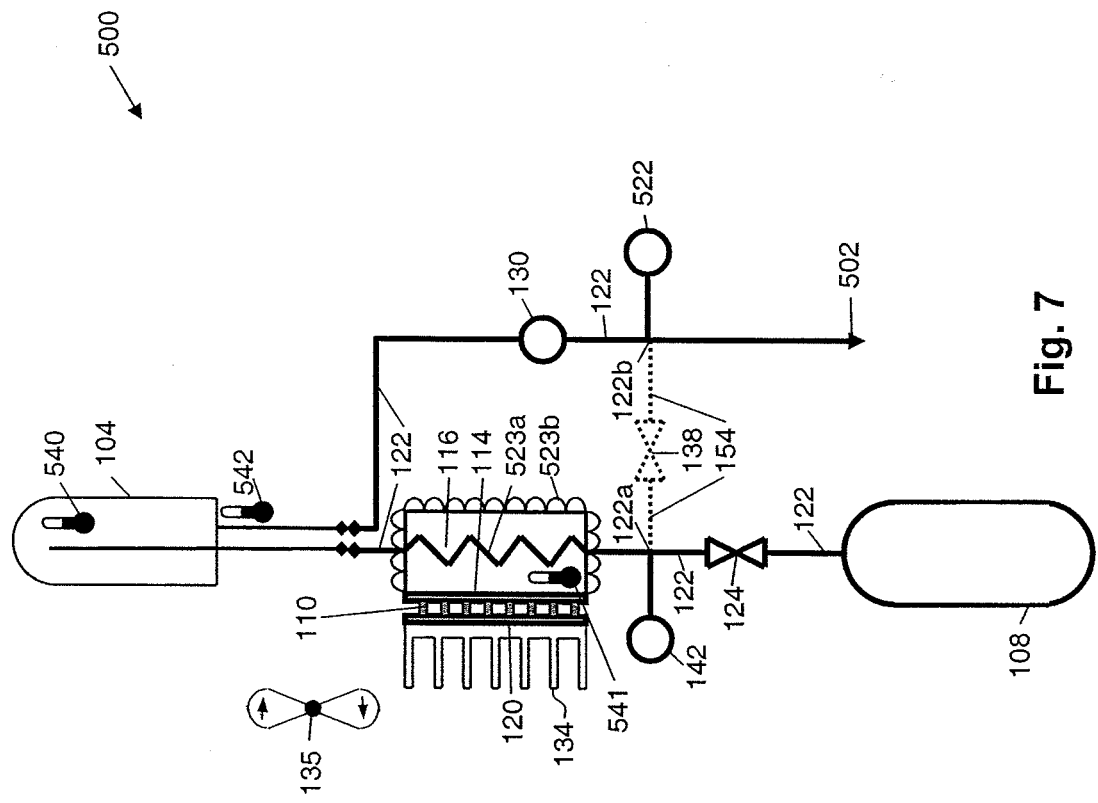
FIG. 7 to FIG. 9 illustrate cryosurgery systems according to exemplary embodiments of the invention.

The embodiment of FIG. 7 further comprises a ventilator 135 for the cooling body. As an alternative to such an air cooler, it is possible to provide a water cooler. Such a member, e.g. the ventilator 135 may transport away heat from the cooling body. Such provisions may be taken as well for the other embodiments disclosed herein.

The particular properties of a thermoelectric cooler can be used for proving an initially higher cooling power which decreases with time. The precool heat exchanger 116 is in contact with the cold side 114 of the thermoelectric cooler 110 and the primary refrigerant used in the ablation device 500. Prior to the freezing cycle the primary refrigerant flow rate is zero and a thermal isolation 523b reduces the heat flow to the ambient. Thus, the thermoelectric device 110 cools the heat exchanger 116 to a low initial temperature. This temperature is measured by a sensor 541. The heat capacity of the heat exchanger 116 serves as a reservoir of low inner energy ("cooling enthalpy storage"). The thermal energy withdrawn from the heat exchanger 116 is conducted to a heat sink 134. Thermal conduction from the heat sink 134 to the ambient can be of any form as for example: free or forced convention, liquid cooling or a heat pipe.

When the ablation is started by opening control valve 124 the primary refrigerant is first effectively cooled. Thus, the ablation device 500 is quickly cooled to its working temperature (without wishing to be bound to a specific theory, it is presently believed that three effects contribute: heat capacity of primary refrigerant, reduced boiling in the supply line, Joule-Thomson coefficient). A rapid freezing at the interface between the ablation probe or catheter 104 and the target tissue (not shown) takes place. During ablation the primary refrigerant flow imposes a thermal load for the precooling device 110.

Thus, the thermoelectric cooler 110 cannot maintain the initially low precooling temperature. The heat capacity of the precool heat exchanger 116 limits the re-warming rate of the precool temperature.

With re-warming of the primary refrigerant in the supply line two effects are observable:

i) Less cooling energy can be obtained from a given mass of the primary refrigerant (FIG. 4, FIG. 5); and ii) The portion of the primary refrigerant which boils out as the pressure drops along the supply line increases (increasing steam quality x). As a consequence the mass flow in the supply line 122 is reduced. Both effects contribute to a decrease in the supplied cooling power. Furthermore, a modest save of the primary refrigerant may be obtained.

On proper dimensioning of the precool device 110 and the heat exchanger 116 the decrease in the supplied cooling power will closely follow the decrease in the heat flow in the ablation device 500 during freezing.

In another embodiment, the warm side 120 of the thermoelectric cooler 110 is thermally connected to the cold side heat exchanger of a Joule-Thomson based secondary cooling system (closed loop or ventilation to air design). For this design very low precooling temperatures are obtained.

Another embodiment is indicated by a bypass stream 154 connecting the high pressure stream 122a and low pressure stream 122b (dashed lines in FIG. 7). When stopping the ablation cycle the supply valve 124 is closed. In addition, bypass valve 138 is opened which connects the high pressure stream 122a of the supply line 122 with the low pressure stream 122b (expanded primary refrigerant). When opening the optional bypass valve 138, the primary refrigerant remaining in the supply line 122 flows directly to the low pressure stream 122b bypassing the ablation catheter 104. This ensures an immediate termination of the ablation procedure.

In the following, a further exemplary embodiment of a cryocatheter system 600 will be explained referring to FIG. 8.

Figure 8:
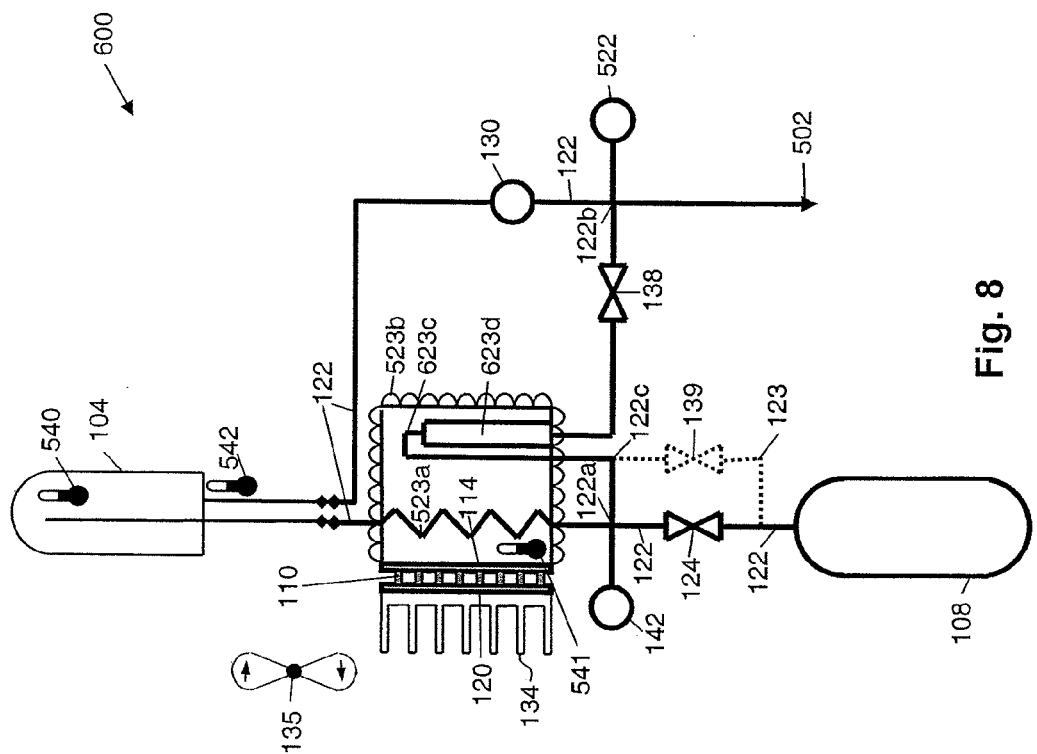

In the modified embodiment of FIG. 8 the bypass flow is guided through an additional fluid pathway 623c incorporated in the precool heat exchanger 116. This pathway 623c contains an expansion element 623d where the bypassed primary refrigerant boils within the heat exchanger 116. The enthalpy of vaporization is withdraw from the heat capacity of the precool heat exchanger 116. Thus, the low initial precool temperature is quickly restored after each ablation cycle.

In yet another embodiment a finite quantity of the primary refrigerant is guided from the fluid tank 108 via an additional pathway 123 including a valve 139 to the fluid pathway 623c before starting the main cooling sequence. Here the additional valve 139 is opened for a short period only for limiting the amount of primary refrigerant flowing through pathway 623c. Note that here valve 138 has to be opened too for allowing for a refrigerant flow. Alternatively valve 138 may be placed between point 122a and 122c simplifying operation. This amount is used for providing the cooling enthalpy stored in the heat exchanger in part or entirely. In this embodiment, the low initial precool temperature is quickly reached. The device is brought to a state were the main cooling unit can be activated with a minimal temporal delay. During the operation of the main cooling unit the additional valve 139 remains closed.

In yet another embodiment the cooling enthalpy is stored in a mass (not shown) which is chilled or frozen in an external cooling device such as a refrigerator (not shown) and thermally connected to the heat exchanger 116 before starting the ablation. Examples for such heat capacities are a frozen mass of ice or a metallic mass.

In yet another embodiment a mass (not shown) which is chilled or frozen in an external cooling device such as a refrigerator (not shown) is thermally connected to the hot side 120 temperature of the thermoelectric cooling device 110 and replaces, thus, the heat sink 134.

The high performance of thermoelectric precooling devices at small temperature differences can be used for a moderate precooling of the primary refrigerant to about 15° C. to 0° C. or less or more particularly to about 12° C. to 6° C. when a simultaneous pressure reduction is carried out (conditioning). If for example nitrous oxide is used as a primary fluid, the high pressure can be reduced to a value between 46 bar and 32 bar or more particularly to a value between 43 bar and 37 bar. In one embodiment the cold side 114 of a thermoelectric cooler 110 is thermally connected with the primary fluid supply line 122 in the vicinity of a pressure reducer 713 (see FIG. 9). Here the pressure can be reduced to a preset value by throttling (essentially isenthalpic process) or in a turbine (essentially isotropic process, the power obtained at the shaft of the turbine may drive a fan for a heat sink). Here the thermal resistance between the outer surface of the supply line 122 and air provides sufficient thermal insulation. In another embodiment an additional insulating layer (not shown) is applied on the supply line.

In the following, a further exemplary embodiment of a cryocatheter system 700 will be explained referring to FIG. 9.

Figure 9:
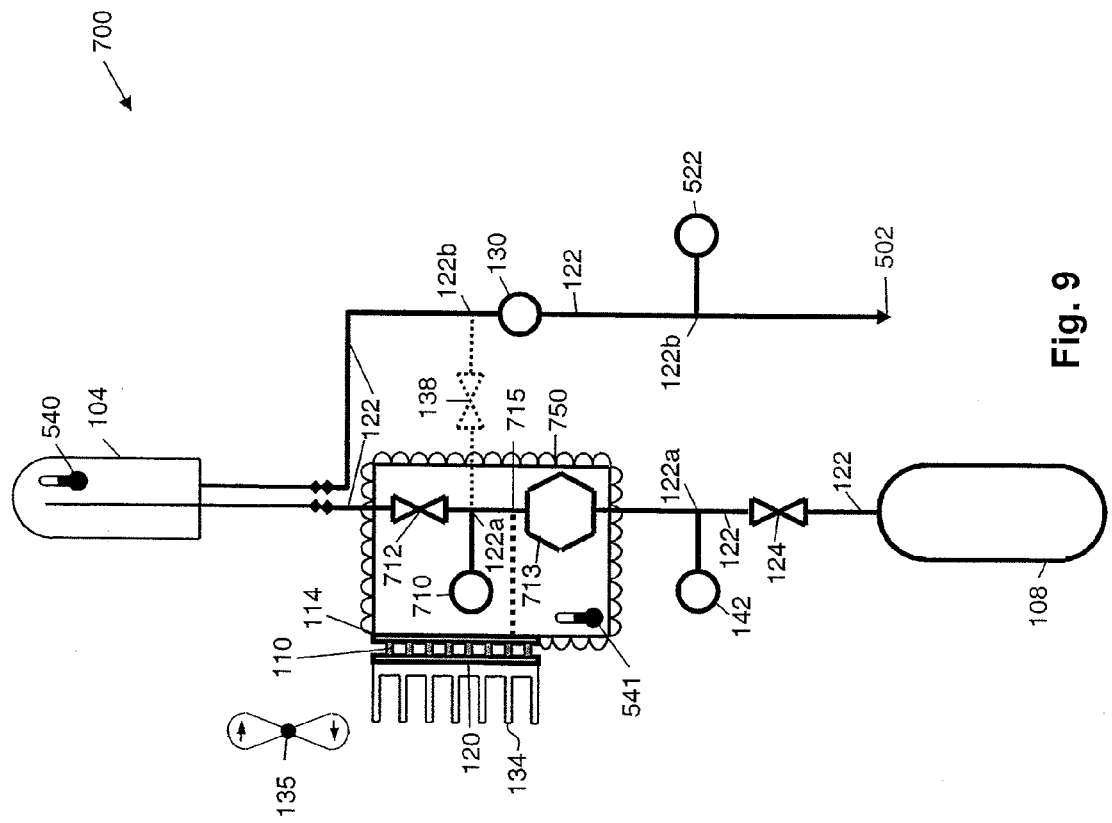

In the embodiment of FIG. 9, a significant portion of the high pressure system including the pressure reducer 713 (and optionally a pressure sensor and/or other components such as valves) is incorporated in a thermally isolating housing 750 and the entire inner space of this housing 750 is cooled to a desired temperature. Here before starting the main cooling sequence by opening valve 712 the main cooling medium is cooled to a temperature below its boiling point at the reduced pressure for ensuring that the fluid is entirely in the liquid phase. Furthermore, also components like the fluid supply line 715, the pressure reducer 713, the pressure sensor 710 or the valve 712 may be cooled to a temperature below the boiling point. Here, a finite cooling enthalpy is stored in the precooled components and the condensed refrigerant.

In one particular embodiment the supply line 715 within the housing is thermally connected to the cold side 114 of the thermoelectric cooler 110 for enabling quick cooling of the line 715 after power on of the system.

In yet another embodiment a significant portion of the high pressure system including the refrigerant supply bottle (not shown) is incorporated in a thermally isolating housing and the entire inner space of this housing is cooled to a desired temperature.

FIG. 9 further shows a further pressure sensor 710 incorporated in the housing 750, and a further valve 712 which is included in the isolated housing 750 as well.

In FIG. 10A to FIG. 10D, an example for an operation mode of the embodiment shown in FIG. 9 is illustrated. Initially at time t41 only the precooling unit is switched on by delivering a current I1 to the thermoelectric cooler 110. The refrigerant in all components between the pressure reducer 713 and the valve 712 along the supply line 715 is cooled below ambient temperature. Similar as for FIG. 3, the initial precooling power is maximal and the desired precooling temperature is reached at t42. The time course of the temperature difference in the precooler ΔT is relatively flat in the zone where gaseous components of the refrigerant condense in the supply line 715 and the precooled components 710, 712, 713. For fastening the condensation process (which contributes to the cooling enthalpy) initially a high current I1 was applied. When the desired temperature minimum $\Delta T_{min}$ is reached, the current is switched to a lower value I2, which is selected such that it is sufficient to maintain the predefined minimal temperature.

At t42' the main cooling sequence is started. The main cooling power at the catheter tip has an initially maximal value as the supplied refrigerant is completely in the liquid phase and the precool temperature is at the minimal value. As the refrigerant flows across the pressure reducer it boils out in part (pressure reduction may be approximated by an isotropic or isenthalpic process in entropy temperature diagram in FIG. 4). This may be compensated entirely or in part by switching the current in the precooler back to a high value I1. As the refrigerant reaches a steady state temperature above the minimum value and as it might contain a remaining gaseous component the steady state cooling power is reduced compared to its initial value.

In FIG. 10B, the stored cooling enthalpy is indicated by a hatched area. Note that for the following precooling and main cooling sequence the process is repeated starting in or after point 43. Only for the very first cooling cycle the starting point 41 is chosen as the system has to be cooled down from ambient temperature to the temperature range of cyclic operation.

FIG. 10C corresponds to FIG. 3C, and FIG. 10D corresponds to FIG. 3D.

In another example for an operation mode the current is not switched between two discrete values but regulated in a continuous way.

Yet another embodiment combines the precooling of a heat exchanger 116 with a specified heat capacity (FIG. 7 and FIG. 8) and precooling with combined pressure reduction (conditioning, FIG. 9).

In an embodiment, a cooling device for cooling a catheter is provided, the cooling device comprising a cooling unit adapted for supplying the catheter with a cooling medium, wherein the cooling unit comprises a cooling loop through which a fluid is guidable as the cooling medium, and a control unit is adapted for controlling an amount of the fluid flowing through the cooling loop based on a value of a temperature sensed in the catheter at a position downstream of a boiling chamber of the catheter. Such an embodiment can be provided with any one of the further features disclosed herein.

In another embodiment, a method of cooling a catheter is provided, the method comprising supplying the catheter with a cooling medium via a cooling loop through which a fluid is guidable as the cooling medium, and controlling an amount of the fluid flowing through the cooling loop based on a value of a temperature sensed in the catheter at a position downstream of a boiling chamber of the catheter. Such an embodiment can be provided with any one of the further features disclosed herein.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

What is claimed is:

1. A cooling device for cooling a catheter, the cooling device comprising
  a main cooling unit adapted for supplying the catheter with a main cooling medium;
  a precooling unit adapted for precooling the main cooling medium before supply of the main cooling medium to the catheter;
  wherein the main cooling unit comprises a cooling pathway through which a fluid is guidable as the main cooling medium;
  the cooling device further comprising a control unit adapted for automatically controlling the main cooling unit and the precooling unit to perform a predetermined cooling procedure, wherein the control unit is adapted for activating the precooling unit before activating a supply of the main cooling medium by the main cooling unit to the catheter;
  a heat exchanger arranged to provide a thermal coupling between the main cooling unit and the precooling unit; and
  a bypass line comprising a valve for selectively connecting a first position of the cooling pathway upstream the precooling unit with a second position of the cooling pathway downstream the catheter so that after terminating supply of the fluid to the catheter, the valve is openable to connect the first position and the second position, wherein the bypass line comprising the valve further comprises a coupling portion which is guided through the heat exchanger;

wherein the control unit is adapted for supplying, after activating, the catheter with a main cooling power having a first value, which is larger than a second value of the main cooling power supplied to the catheter at a later stage, wherein the cooling device is adapted to adjust the precooling to be more efficient at a beginning than at a later stage, and wherein the precooling unit comprises a thermoelectric cooling element.

2. The cooling device of claim 1,
wherein the precooling unit is free of a cooling loop through which a fluid is guidable.

3. The cooling device of claim 1,
wherein the thermoelectric cooling element comprises a Peltier element.

4. The cooling device of claim 1, comprising
a thermal insulator surrounding at least a part of the heat exchanger; and
a pressure system adapted for providing pressure for transporting the main cooling medium along the cooling device;
wherein at least a part of the pressure system is accommodated within the thermal insulator.

5. The cooling device of claim 4, wherein a pressure reducer of the pressure system is accommodated within the thermal insulator.

6. The cooling device of claim 1,
wherein the coupling portion comprises an expansion element for an expansion of main cooling medium expanding from the coupling portion into the expansion element.

7. The cooling device of claim 1,
wherein the heat exchanger is made of a material having a thermal capacity in a range between 1.5 J/K and 1500 J/K.

8. The cooling device of claim 1,
wherein the control unit is adapted for enabling activation of the main cooling unit by a user only when a temperature of the heat exchanger achieved by the precooling has fallen below a predefined value.

9. The cooling device of claim 1,
wherein the control unit is adapted for supplying the main cooling medium with a variable main cooling power by storage of cooling enthalpy;
wherein the control unit is adapted for storing this cooling enthalpy before activation of the main cooling unit.

10. The cooling device claim 1,
wherein the control unit is adapted for controlling a current flow through the thermoelectric cooling element to thereby modify a precooling power over time.

11. The cooling device of claim 10, comprising one of the following features:

the control unit is adapted for switching a current supplied to the thermoelectric cooling element between discrete values;
the control unit is adapted for continuously regulating a current supplied to the thermoelectric cooling element.

12. The cooling device of claim 1,
adapted to be operable in a manner that at least a part of cooling enthalpy provided by the precooling unit during the precooling is stored in a condensation of the main cooling medium before starting the main cooling.

13. The cooling device of claim 1,
wherein a warm side of the thermoelectric cooling element is coupled to a closed loop cooling unit.

14. The cooling device of claim 1,
wherein a cooling enthalpy is supplied from a main refrigerant tank via a supply line containing a valve;
whereas the valve is activatable for storing the cooling enthalpy before activating a main cooling cycle;
wherein the valve remains closed during the main cooling cycle.

15. A cryosurgery system, comprising
a catheter;
a cooling device of claim 1 for cooling the catheter.

16. The cooling device of claim 1, wherein a precooling of the heat exchanger with a specified heat capacity is combined with a precooling with a combined pressure reduction.

17. A method of cooling a catheter, the method comprising
supplying the catheter with a main cooling medium;
precooling the main cooling medium with a precooling unit before supplying the main cooling medium to the catheter;
guiding a fluid as the main cooling medium through a cooling loop;
activating the precooling before activating a supply of the main cooling medium to the catheter;
providing a heat exchanger arranged to provide a thermal coupling between a main cooling unit and the precooling unit;
after terminating a supply of the fluid to the catheter, selectively connecting a first position of a cooling pathway upstream the precooling unit with a second position of the cooling pathway downstream the catheter with a valve in a bypass line and bypassing the first position and the second position, wherein the bypass line comprises a coupling portion which is guided through the heat exchanger;
wherein a first value of a main cooling power is supplied to the catheter after activating, the first value being larger than a second value of the main cooling power supplied to the catheter at a later stage;
wherein the precooling is more efficient at a beginning than at a later stage, and wherein the precooling unit comprises a thermoelectric cooling element.

* * * * *